United States Patent
Fabrizio

(10) Patent No.: US 9,305,141 B2
(45) Date of Patent: Apr. 5, 2016

(54) METHOD, SYSTEM AND PROGRAM PRODUCT FOR IDENTIFYING A USER ON AN EXERCISE EQUIPMENT

(75) Inventor: Giudici Fabrizio, Bologna (IT)

(73) Assignee: Technogym S.p.A., Gambettola (IT)

( * ) Notice: Subject to any disclaimer, the term of this patent is extended or adjusted under 35 U.S.C. 154(b) by 649 days.

(21) Appl. No.: 13/419,025

(22) Filed: Mar. 13, 2012

(65) Prior Publication Data

US 2013/0241696 A1     Sep. 19, 2013

(51) Int. Cl.
*G05B 19/00*     (2006.01)
*G06F 19/00*     (2011.01)
*A63B 24/00*     (2006.01)
*A63B 71/06*     (2006.01)

(52) U.S. Cl.
CPC ........ *G06F 19/3481* (2013.01); *A63B 24/0087* (2013.01); *A63B 71/0622* (2013.01); *A63B 2225/096* (2013.01); *A63B 2225/15* (2013.01); *A63B 2225/20* (2013.01); *A63B 2225/50* (2013.01); *A63B 2225/54* (2013.01)

(58) Field of Classification Search
CPC ............ G06F 19/3481; A63B 2225/50; A63B 2225/20; A63B 2225/54; A63B 2225/096; A63B 2225/15; A63B 24/0087; A63B 71/0622
See application file for complete search history.

(56) References Cited

U.S. PATENT DOCUMENTS

| | | | |
|---|---|---|---|
| 6,601,016 B1 * | 7/2003 | Brown et al. | 702/182 |
| 6,702,719 B1 * | 3/2004 | Brown et al. | 482/8 |
| 6,746,371 B1 * | 6/2004 | Brown et al. | 482/8 |
| 7,507,183 B2 | 3/2009 | Anderson et al. | |
| 7,988,598 B2 | 8/2011 | Trzecieski | |
| 8,529,409 B1 * | 9/2013 | Lesea-Ames | 482/9 |
| 2007/0201727 A1 | 8/2007 | Birrell et al. | |
| 2009/0219159 A1 * | 9/2009 | Morgenstern | 340/573.1 |
| 2011/0010188 A1 * | 1/2011 | Yoshikawa et al. | 705/2 |
| 2012/0309192 A1 * | 12/2012 | Wang et al. | 438/669 |

* cited by examiner

*Primary Examiner* — Ojiako Nwugo
(74) *Attorney, Agent, or Firm* — Blank Rome LLP

(57) ABSTRACT

A method, a system and a program product for identifying a user on a exercise equipment. An equipment identification code associated to a exercise equipment is acquired by means of an electronic portable device of the user. The equipment identification code and the user identification code are sent, by means of the electronic portable device, to an electronic calculator operatively connected to the exercise equipment.

20 Claims, 2 Drawing Sheets

METHOD, SYSTEM AND PROGRAM PRODUCT FOR IDENTIFYING A USER ON AN EXERCISE EQUIPMENT

FIELD OF THE DISCLOSURE

The present disclosure relates to the fitness industry, particularly, to a method and system for identifying a user on an exercise equipment.

BACKGROUND

Nowadays, in order to execute a training on a specific exercise equipment chosen on the basis of a training program or physical exercise to be executed by an user, the user needs to be identified on such exercise equipment.

Such identification procedure can be performed by the user on an electronic calculator of the health or fitness centre, operatively connected to all the exercise equipments, or directly on the exercise equipment chosen by the user.

Once the user identification procedure is completed, a specific training or exercise program for the user can be loaded by the chosen exercise equipment from a server remotely or locally connected to the exercise equipment.

The identification procedure can be manually performed by the user which inserts a user login and a password by means of a touchscreen user interface of the exercise equipment or by means of input interface (i.e. the keyboard and/or the mouse) of the electronic calculator of the fitness centre. Alternatively, the user can provide the exercise equipment or the electronic calculator of the fitness centre with their own user identification data by inserting a supporting data portable device (i.e. an electronic key), storing such user identification data, in a corresponding slot of the exercise equipment or the electronic calculator of the fitness centre via a communication interface (i.e. of the RFID or USB type).

The above described user identification procedure offers several disadvantages.

Firstly, it is required to the user to remember or to annotate on some supports (i.e. onto the agenda, a leaflet, a portable device, and so on) the user login and password. Secondly, such authentication procedure is not intuitive for that group of people, especially elder people, who are not familiar with the new technology devices (i.e. a touchscreen user interface of the exercise equipment or simply an electronic calculator).

By contrast, providing the user with a supporting data portable device storing the user authentication data avoids the need for the user to remember the user login and password. However, according to this solution, the identification procedure can be only performed using the supporting data portable device and, therefore, the user has to bring with themselves to the health or fitness centre such portable device. In addition, the supporting data portable device constitutes a further portable device or object, in addition to mobile phones, PAD (Personal Digital Assistant), notebook, tablet, home or car key, and so on, which the user has to bring with themselves during the day and that it could be easily forgotten on the desk or even lost or stolen. Furthermore, in this solution, the exercise equipment or the electronic calculator of the fitness centre needs to be provided with the slot to receive and to be configured to read the user authentication data from the supporting data portable device.

SUMMARY OF THE INVENTION

According to some aspects of the present description, a method for identifying a user on an exercise equipment is provided with allows to overcame the drawbacks mentioned above with reference to the prior art and particular which results more simple in order to be also used by the people that are less familiar with the new technology devices.

According to a first aspect, there is provided a method for identifying a user on a exercise equipment comprising: acquiring, by means of an electronic portable device of the user, an equipment identification code associated to a exercise equipment; sending, by means of the electronic portable device, the equipment identification code to an electronic calculator; sending, by means of the electronic portable device, the user identification code to the electronic calculator.

According to a second aspect, there is provided a system for identifying a user on a exercise equipment, comprising: an exercise equipment having a respective equipment identification code; a electronic calculator operatively connected to the exercise equipment; a electronic portable device comprising a user identification code, the electronic portable device being configured to acquire the equipment identification code from the exercise equipment. The electronic portable device is further configured to send the equipment identification code to the electronic calculator and to send the user identification code to the electronic calculator.

According to a third aspect, there is provided a program product loadable in a memory unit of an electronic portable device of a user, the program product being executed by a data processing unit of the electronic portable device to perform: acquiring an equipment identification code associated to a exercise equipment; sending the equipment identification code to a electronic calculator; sending the user identification code to the electronic calculator.

According to a fourth aspect, it is provided a program product loadable in a memory unit of a electronic calculator, the program product being executed by a data processing unit of the electronic calculator to perform sending to an exercise equipment, on the basis of both an equipment identification code associated to an exercise equipment and an user identification code, user operative data.

Further aspects are provided in the description, drawings and claims of the present application.

BRIEF DESCRIPTION OF THE DRAWINGS

Further features and advantages of the method and system according to the present disclosure will appear more clearly from the following description of preferred embodiments thereof, given by way of a non-limiting example with reference to the annexed figures, wherein.

DETAILED DESCRIPTION OF THE PREFERRED EMBODIMENTS

With reference to the embodiment of FIG. 1, a system 100 for identifying a user on a exercise equipment, hereinafter also referred to simply as system 100, is now described.

The system 100 comprises a exercise equipment 101.

It should be noted that, according to the present disclosure, exercise equipment means any equipment, machine or apparatus which can be used by a user for executing training or exercise program, having electronic on board, as it will be clearly explained in the following. Examples of such exercise equipment can be a cardio training machine like a treadmill, a bike, a spinning machine, and so on, or a strength training machine like a chest press, a shoulder press, a leg press and so on.

Figure 1:
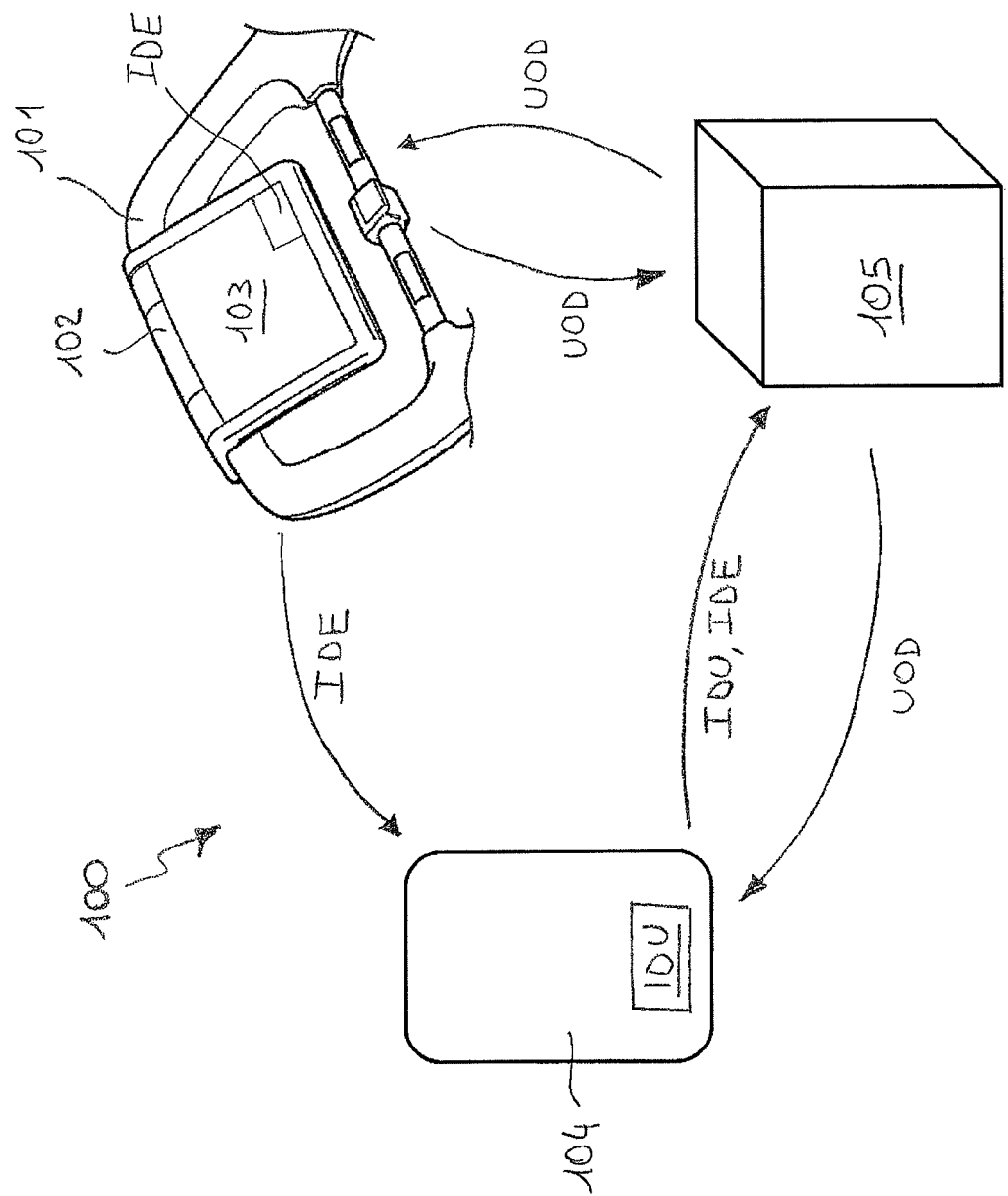
FIG. 1 shows a schematic view of a system for identifying a user on a exercise equipment according to an embodiment of the disclosure.

It should be observed that in the embodiment of the FIG. 1 the equipment machine is represented as a portion of a treadmill, in order to better highlight the technical features of the equipment which are more important for the present disclosure.

In greater detail, the exercise equipment 101 comprises a control station 102 having a data processing unit and memory unit (both not shown in the FIG. 1). The memory unit is configured to store both a program product (e.g. a program code) to allow the exercise equipment 101 to manage the training of a user and the data processed by the data processing unit during the operation of the exercise equipment 101.

The control station 102 further comprises a display 103 and a control module (the last one not indicated in the FIG. 1), e.g. a touchscreen interface, configured to allow the user to interact with the exercise equipment 101.

It should be observed that in the embodiment of the FIG. 1 the control module is a touchscreen interface and therefore it corresponds to the display 103 of the control station 102 of the exercise equipment 101.

The exercise equipment 101 further comprises an equipment identification code IDE.

Such an equipment identification code IDE can be, for example, an alphanumerical character string, a one-dimensional bar code, a bi-dimensional bar code (also known as QR code), and so on. Alternatively to or in s combination with such examples of equipment identification code, the user identification code can be also, for example, a tag of the RFID technology, a tag of the NFC (Near Field Communication) technology, or a tag of any other technology compatible with the NFC technology, and so on.

It should be noted that the equipment identification code IDE (of the first list of examples or of the second list of examples listed above or both of them) can also comprise the serial number of the exercise equipment 105. Such information advantageously allows a electronic calculator 105, described in the following, to control additional information of the exercise equipment 105, e.g. if the equipment is original or counterfeited, the position of the equipment, data representative of the operative life of the equipment.

The equipment identification code IDE can be shown by the control station 102 on the display 103 when the exercise equipment 101 operates. Alternatively or in addition, the equipment identification code IDE can be directly applied, e.g. in the form of a stick, onto a portion of the exercise equipment 101, e.g. onto a portion of the display 103 of the control station 102 or onto a supporting handle of the exercise equipment 101.

In the embodiment of FIG. 1, the equipment identification code IDE is schematically represented as applied onto a portion of the display 103 of the control station 102 of the exercise equipment 101.

With reference again in general to the embodiment of FIG. 1, the system 100 further comprises an electronic portable device 104 of the user.

According to the present disclosure, for electronic portable device it is meant a mobile phone (e.g. a smartphone), a digital audio/video file reader (e.g. a MP3 reader), a tablet, and so on.

The electronic portable device 104 (e.g. a smartphone), comprises a data processing unit, a memory unit, a display and a control module to allow the user to use the electronic portable device, e.g. a touchscreen interface, at least one of a camera, reader of bar codes or a tag reader, of the RFID or NFC technology or any other technology compatible with the NFC technology, not shown in FIG. 1.

In greater detail, it should be noted that the memory unit of the electronic portable device 104 is configured to store program products (e.g. a program codes) to allow the electronic portable device 104 to execute several applications which can be required by the user. In particular, the memory unit is configured to store a program product to allow the electronic portable device 104, on request of the user, to perform a method for identifying a user on an exercise equipment, as it will be described in the following.

In this regard, the electronic portable device 104 comprises, stored in the memory unit, a user identification code IDU, schematically shown in the FIG. 1. As an example, the user identification code IDU is an alphanumerical character string.

In addition, the electronic portable device 104 is configured to acquire, e.g. by means of at least one of the camera, the reader of bar codes or the tag reader, the equipment identification code IDE from the exercise equipment 101.

Furthermore, the electronic portable device 104 is configured to send the equipment identification code IDE to an electronic calculator 105, by means of a communication network, e.g. Internet.

In addition, the electronic portable device 104 is configured to send the user identification code IDU to the electronic calculator 105, by means of the same communication network.

It should be noted that, according to an embodiment, the electronic device 104 can be configured to send the equipment identification code IDE separately from the user identification code IDU. In accordance to another embodiment, the electronic device 104 can be configured to send the equipment identification code IDE together with the user identification code IDU.

With reference again to the embodiment of FIG. 1, the system 100 further comprises such an electronic calculator 105, e.g. a server computer, remotely or locally disposed with respect to the health or fitness centre in which the exercise equipment 101 and the user with the electronic portable device 104 are present.

The electronic calculator 105 is operatively connected to all the exercise equipment of the health or fitness centre and therefore it is operatively connected to the exercise equipment 101. As an example, the electronic calculator 105 is operatively connected to the exercise equipment 101 by means of a communication network, e.g. wired communication network or a wireless communication network.

The electronic calculator 105 comprises a data processing unit and a memory unit (both not shown in FIG. 1).

In greater detail, it should be observed that the memory unit of the electronic calculator 105 is configured to store a program product (e.g. instructions code) to allow the electronic calculator 105 to perform the method for identifying a user on a exercise equipment, as it will be described in the following.

In greater detail, the electronic calculator 105 is configured to send to the exercise equipment 101, on the basis of both the equipment identification code IDE associated to said exercise equipment 101 and the user identification code IDU, user operative data UOD.

In such a way, the user is identified on the exercise equipment 101 chosen by the user themselves to be used for the training program. The exercise equipment 101 can be configured to show on the display 103 of the control station 102 the user operative data UOD. Before or during showing the user operative data, the exercise equipment 101 can be configured to show a welcome message for the user also reporting the name of the identified user.

The electronic calculator 105 is also configured to receive from the exercise equipment 101, on the basis of both the equipment identification code IDE associated to said exercise equipment 101 and the user identification code IDU, such user operative data UOD.

According to the present disclosure, the user operative data UOD are user personal data UDP, updated user personal data UUDP, the training program TP, training data TD and archive personal data APD. Each of them will be defined in the following of the present disclosure.

When the user identification is completed, the exercise equipment 101 is ready to be directly set up by the user with the proper training program by means of the interactive user interface of the control station 102 of the exercise equipment 101.

As an alternative, the electronic calculator 105 can be configured to store, within the proper memory unit, for each of the users subscribed to the health or fitness centre, the respective training program TP assigned and customized for the user.

According to the present disclosure, the training program TP is, for example, a list of exercises to be executed on the exercise equipment one or more of them can be selected from the list, by means of the control module (e.g. a touchscreen interface) of the control station 102 of the exercise equipment 101, by the user. In a further example, the training program TP corresponds to control signals to automatically set up the exercise equipment on the basis of the training program customized for the user.

In particular, the electronic calculator 105 is configured to send to the exercise equipment 101, on the basis of both the equipment identification code IDE associated to said exercise equipment 101 and the user identification code IDU received from the electronic portable device 104 associated to the equipment identification code IDE, the respective training program TP assigned to the user having the user identification code IDU.

According to such embodiment, when the user identification procedure is completed, the exercise equipment 101 is configured both to show on the display 103 of the control station 102 the training program TP of the user and to set up such training program of the user.

With reference again to the electronic calculator 105, according to a further embodiment, it can be also configured to send to the electronic portable device 104, on the basis of the equipment identification code IDE, equipment instruction data EID, i.e. audio or video file explaining how the exercise equipment 101 operates.

In a corresponding way, the electronic portable device 104 can be configured to receive from to the electronic calculator 105, on the basis of the equipment identification code IDE, the equipment instruction data EID, i.e. audio or video file explaining how the exercise equipment 101 operates.

According to a further embodiment, the exercise equipment 101 is configured to send to the electronic calculator 105, on the basis of the user identification code IDU, training data TD of the user.

According to a further embodiment, also the electronic portable device 101 is configured to send to the electronic calculator 105, on the basis of both the equipment identification code IDE and the user identification code IDU, training data TD of the user.

According to the present disclosure, the training data TD of the user can be partial or complete training data of the training program TP in execution or executed by the user, also in the form of simple answers given by the user to questions shown on the display of the exercise equipment 105 or the electronic portable device 104, e.g. "how long have you been using the exercise equipment?", "how many times did you repeat the exercise on the exercise equipment?", and so on.

In this regard, the electronic calculator 105 can be configured to store, into an area of the memory unit which is reserved to the user having the user identification code IDU, such training data TD of the user.

In addition, the electronic calculator 105 is configured to send to the electronic portable device 104 of the user, by means of a communication network (e.g. Internet), on the basis of the user identification code IDU, such training data TD of the user.

In a corresponding way, the electronic portable device 104 is further configured to receive from the electronic calculator 105, on the basis of both the equipment identification code and the user identification code, the user operative data UOP, e.g. at least one of user personal data UPD or training data TD or both of them.

Furthermore, the electronic calculator 105 can be advantageously configured to store, into an area of the memory unit which is reserved to the user having the user identification code IDU, also user personal data UPD.

According to the present disclosure, the user personal data UPD are data corresponding to entertainment activities performed by the user in addition or together with performing the training program TP, such as "favorite" websites consulted by the user during the navigation on Internet, favorite music, favorite films or TV channels, and so on.

In this regard, referring back to the exercise equipment according to the embodiments previously described, it should be observed that it is also configured to allow the user to perform, in addition and together with performing the training program TP, entertainment activities such as navigating on Internet, listening to music, watching the TV, and so on, corresponding to provide to the control station 102 of the exercise equipment 101 updated user personal data UUPD.

In addition, the exercise equipment 101 is also configured to allow the user to change such user personal data UPD by means of the interactive user interface of the control station 102 of the exercise equipment 101.

Furthermore, the exercise equipment 101 is also configured to send to the electronic calculator 105, on the basis of the user identification code IDU, the user personal data UPD in order to the user personal data UPD can be stored into the area of the memory unit of the electronic calculator 105 which is reserved to the user having the user identification code IDU.

In addition, the exercise equipment 101 is further configured to send to the electronic calculator 105, on the basis of the user identification code IDU, the updated user personal data UUPD in order to the updated user personal data UUPD can be stored into the area of the memory unit of the electronic calculator 105 which is reserved to the user having the user identification code IDU.

In a corresponding way, the electronic calculator 105 is further configured to receive from the electronic portable device 104, on the basis of both the equipment identification code IDE and the user identification code IDU, updated user personal data UUPD.

In addition, the electronic calculator 105 is configured to perform also the step of receiving from the electronic portable device 104, on the basis of both the equipment identification code IDE and the user identification code IDU, training data TD of the user.

With reference again to the electronic calculator 105, it can be further configured to store, into an area of the memory unit which is reserved to the user having the user identification code IDU, also archive personal data APD.

In addition, the electronic calculator 105 is configured to send to the exercise equipment 101, on the basis of the user identification code IDU, the archive personal data APD.

Moreover, the electronic calculator 105 can be also configured to send to the electronic portable device 104, on the basis of the user identification code IDU, the archive personal data APD.

According to the present disclosure, the archive personal data APD are the user operative data UOD related to the past training program executed and the past activities performed by the user on the exercise equipments of the fitness center.

Figure 2:
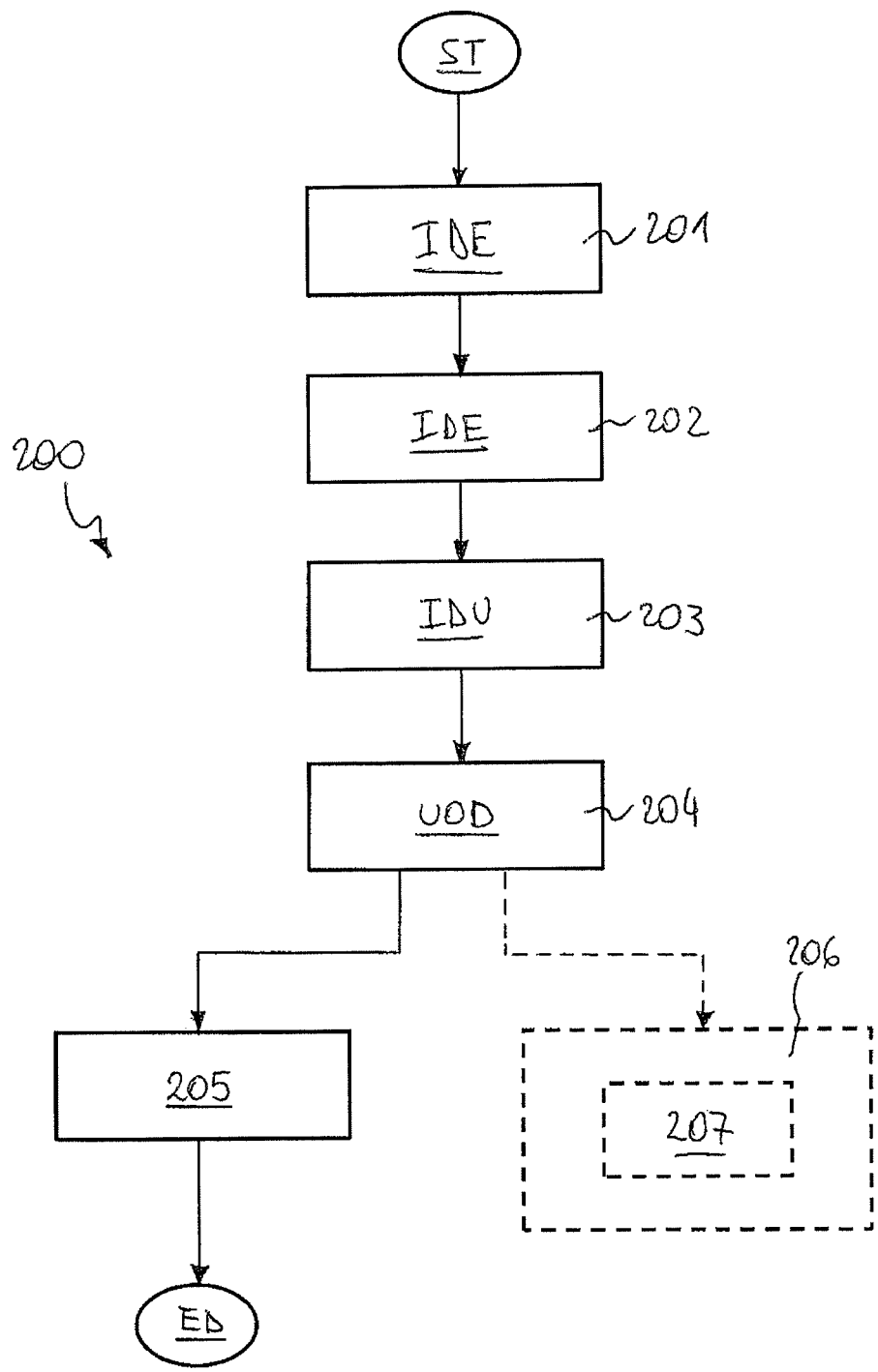
FIG. 2 shows a block diagram of a method for identifying a user on a exercise equipment according to an embodiment of the disclosure.

With reference again to FIG. 1 and in particular to the block diagram of FIG. 2, a method for identifying a user on a exercise equipment according to an embodiment of the disclosure is now described.

The method 200 for identifying a user on an exercise equipment 101, in the following simply method 200, comprises a symbolic step of start ST.

The method 200 further comprises a step acquiring 201, by means of an electronic portable device 104 of the user, an equipment identification code IDE associated to a exercise equipment 101. In particular, the step of acquiring 201 can be performed by shooting a digital photo of the equipment identification code IDE by means of the camera of the electronic portable device 104. Alternatively, the step of acquiring 201 can be performed by at least one of catching the image of the equipment identification code IDE by means of the camera of the electronic portable device 104, reading the bar code by means of the reader of bar codes of the electronic portable device 104 or reading a tag (of the RFID or NFC technology or any other technology compatible with the NFC technology) by means of the tag reader of the electronic portable device 104.

Subsequently, the method 200 comprises the step of sending 202, by means of the electronic portable device 104, the equipment identification code IDE to an electronic calculator 105.

The method 200 further comprises a step of sending 203, by means of the electronic portable device 104, the user identification code IDU to the electronic calculator 105. As previously mentioned, the user identification code IDU is stored in the electronic portable device.

In this regard, it should be noted that the user identification code IDU is provided to the electronic portable device 104 by the user when the program product loaded in the electronic portable device 104 to perform a method 200 is executed by the user for the first time. As an example, the user identification code IDU can be provided to the electronic portable device 104 by the user inserting login and password in response to a request of the program product executed for the first time.

According to an embodiment of the disclosure, the step of sending 202 the equipment identification code IDE is performed separately from the step of sending 203 the user identification code IDU are performed subsequently one another.

According to a another embodiment of the disclosure, the step of sending 202 the equipment identification code IDE is performed with the step of sending 203 the user identification code IDU.

Turning to FIG. 2, the method 200 further comprises a step of sending 204, by means of the electronic calculator 105, on the basis of both the equipment identification code IDE associated to said exercise equipment 101 and the user identification code IDU, user operative data UOD to an exercise equipment 101. The user operative data UOD have been previously defined.

In addition, the method 200 further comprises the step of manually setting up, by the user, a training program TP on the exercise equipment 101 on which the user has been identified.

The method 200 ends with a symbolic step of end ED.

According to a further embodiment, indicated with a dotted line in the block diagram of FIG. 2, the method 200, alternatively to the step of manually setting up 205, can comprise a step of automatically setting up 206, by means of the exercise equipment 101, a training program TP of the user, associated with the user identification code IDU, received from the electronic calculator 105.

In greater detail, the step of automatically setting up 206 comprises the step of sending 207 to the exercise equipment 101, by means of the electronic calculator 105, on the basis of the equipment identification code IDE associated to the exercise equipment 101 and of the user identification code IDU received from the electronic portable device 104 associated to the equipment identification code IDE, the respective training program TP assigned to the user having the user identification code IDU.

On this purpose, as already previously indicated, the electronic calculator 105 can be configured to store within the proper memory unit associating to each of the users subscribed to the health or fitness centre the respective training program TP assigned by a personal trainer.

According to such further embodiment, the method 200 ends with the symbolic step of end ED.

According to a further embodiment, not shown in the figure, the method 200 can comprise the following steps, which can be considered in combination with the steps previously described.

The method 200 comprises the step of sending to the electronic calculator 105, on the basis of the user identification code IDU, training data TD of the user. It should be observed that the training data TD of the user are partial or complete data of the training program TP in execution or executed by the user.

In addition, the method 200 further comprises the step of storing, by means of the electronic calculator 105, such training data TD into an area of the memory unit of the electronic calculator 105 which is reserved to the user having the user identification code IDU.

Furthermore, the method 200 comprises the step of sending to the electronic portable device 104 of the user, by means of the electronic calculator 105, on the basis of the user identification code IDU, such training data TD of the training program in execution or executed by the user. The training data TD have been previously defined.

According to a further embodiment, the method 200 can comprise the step of sending to the electronic calculator 105, by means of the electronic portable device 101, on the basis of both the equipment identification code IDE and the user identification code IDU, training data TD of the user.

Furthermore, the method 200 comprises the step of sending to the exercise equipment 101, be means of the electronic calculator 105, on the basis of the user identification code IDU, user personal data UPD. Also the user personal data UPD have been previously defined.

In this regard, as previously indicated, such user personal data UPD are stored into an area of the memory unit of the electronic calculator 105 which is reserved to the user having the user identification code IDU. The user personal data correspond to entertainment activities performed by the user in addition or together with performing the training program TP, such as "favorite" websites consulted by the user during the navigation on Internet, favorite music, favorite films or TV channels, and so on.

In addition, the method 200 comprises the step of updating, by means of the electronic calculator 105, on the basis of the user identification code IDU, the user personal data UPD. In fact, as previously described, the user can change the user personal data UPD by means of the interactive user interface of the control station 102 of the exercise equipment 101.

In particular, the step of updating further comprises the step of sending to the electronic calculator 105, by means of the exercise equipment 101, on the basis of the user identification code IDU, the user personal data UPD.

With reference again to the method 200, it can further comprise the step of sending to the exercise equipment 101, by means of the electronic calculator 105, on the basis of the user identification code IDU, archive personal data APD. Such archive personal data APD have been previously defined.

In addition, the method 200 can further comprise the step of sending to the electronic portable device 104, by means of the electronic calculator 105, on the basis of the user identification code IDU, the archive personal data APD.

Furthermore, the method 200 can comprise the step of sending to the electronic portable device 104, by means of the electronic calculator 105, on the basis of the equipment identification code IDE, equipment instruction data EID, i.e. audio or video file explaining how the exercise equipment 101 operates.

According to a further embodiment of the disclosure, a program product can be loaded in the memory unit of the electronic portable device 104 of a user. The program product can be executed by the data processing unit of the electronic portable device 104 to perform the following steps:

acquiring 201 an equipment identification code IDE associated to a exercise equipment 101;

sending 202 the equipment identification code IDE to an electronic calculator 105;

sending 203 the user identification code IDU to the electronic calculator 105.

With reference to the step of acquiring 201, the program product can be executed by the data processing unit of the electronic portable device 104 to perform at least one of shooting a digital photo of the equipment identification code IDE by means of the camera of the electronic portable device 104, catching the image of the equipment identification code IDE by means of the camera of the electronic portable device 104, reading the bar code by means of the reader of bar codes of the electronic portable device 104 or reading a tag (of the RFID or NFC technology or any other technology compatible with the NFC technology) by means of the tag reader of the electronic portable device 104.

The program product can be executed by the data processing unit of the electronic portable device 104 to perform also the step of requesting to the user, when the program product is executed by the user for the first time, the user identification code IDU (e.g. login and password).

In addition, the program product can be executed by the data processing unit of the electronic portable device 104 to perform also the step of receiving from the electronic calculator 105, on the basis of both the equipment identification code IDE and the user identification code IDU, user operative data UOD (e.g. user personal data UPD, training data TD, and so on).

Furthermore, the program product can be executed by the data processing unit of the electronic portable device 104 to also perform the step of receiving from to the electronic calculator 105, on the basis of the equipment identification code IDE, the equipment instruction data EID, i.e. audio or video file explaining how the exercise equipment 101 operates.

According to another embodiment of the disclosure, a program product can be loaded in the memory unit of the electronic calculator 105. The program product can be executed by the data processing unit of the electronic calculator 105 to perform the step sending 204, on the basis of both the equipment identification code IDE associated to the exercise equipment 101 and the user identification code IDU, user operative data UOD, previously described.

In addition, the program product can be executed by the data processing unit of the electronic calculator 105 to perform the step of sending 207 to the exercise equipment 101, on the basis of the equipment identification code IDE associated to the exercise equipment 101 and of the user identification code IDU received from the electronic portable device 104 associated to the equipment identification code IDE, a training program TP assigned to the user having the user identification code IDU.

Furthermore, the program product can be executed by the data processing unit of the electronic calculator 105, to perform the steps of:

sending to the exercise equipment 101, on the basis of the user identification code IDU, user personal data UPD;

updating, on the basis of the user identification code IDU, the user personal data UPD as received from the exercise equipment 101, said user personal data UPD being stored into an area of the memory unit of the electronic calculator 105 which is reserved to the user having the user identification code IDU.

The user personal data UPD, already previously described, are stored into an area of the memory unit of the electronic calculator 105 which is reserved to the user having the user identification code IDU.

The program product can be executed by the data processing unit of the electronic calculator 105 to perform the step of receiving from the electronic portable device 104, on the basis of both the equipment identification code IDE and the user identification code IDU, updated user personal data UUPD.

Furthermore, the program product can be executed by the data processing unit of the electronic calculator 105 to perform also the step of receiving from the electronic portable device 104, on the basis of both the equipment identification code IDE and the user identification code IDU, training data TD of the user.

Furthermore, the program product can be executed by the data processing unit of the electronic calculator 105, to perform the step of sending to the electronic portable device 104 of the user, on the basis of the user identification code IDU, training data TD of the user. It should be noted that the training data TD of the user are partial or complete data of the training program in execution or executed by the user.

Furthermore, the program product can be executed by the data processing unit of the electronic calculator 105 to perform the step of sending to the electronic portable device 104, on the basis of the equipment identification code IDE, equipment instruction data EID, i.e. audio or video file explaining how the exercise equipment 101 operates.

According to a further embodiment of the disclosure, a program product can be loaded in a memory unit of the exercise equipment 101. The program product can be executed by the data processing unit of the exercise equipment 101 to perform the following steps:

sending to the electronic calculator 105, on the basis of the user identification code IDU, training data TD of the user;

sending to the electronic calculator 105, on the basis of the user identification code IDU, the user personal data UPD.

The method for identifying a user on a exercise equipment according to the present disclosure allows the user to be identified on the exercise equipment in a quick and simple manner.

In fact, the identification on the exercise equipment is performed by the user simply launching a program product on the electronic portable device (e.g. a mobile phone or smartphone) which allows the user to identify themselves on the exercise machine after simply acquiring the equipment identification code of the chosen exercise equipment. The acquisition of the equipment identification can be obtained, for example, by at least one of shooting a digital photo of the equipment identification code by means of the camera of the electronic portable device, catching the image of the equipment identification code IDE, reading a bar code by means of the reader of bar codes or reading a tag (of the RFID or NFC technology or any other technology compatible with the NFC technology), by means of the tag reader of the electronic portable device 104.

In view of this identification procedure, there is no need for the user to remember or annotate any user login and password onto be provided with any additional portable devices other than their mobile phone.

In addition, according to a further embodiment of the disclosure, thanks to the user identification code associated to the equipment identification code, the electronic calculator is able to send to the exercise equipment the training program and user personal data of the user identified on a specific exercise equipment.

Furthermore, according to a further embodiment of the description, thanks to the user identification code associated to the equipment identification code, the exercise equipment is advantageously able to send to the electronic calculator complete or partial data of the training program in execution or executed by the user. The electronic calculator is also able to send the complete or partial data of the training program in execution or executed by the user to the electronic portable device of the user.

According to some embodiments of the present description, thanks to the user identification code associated to the equipment identification code, the exercise equipment and the electronic calculator are able to share and update user personal data of the user.

A man skilled in the art may make several changes, adjustments and replacements of elements with other functionality equivalent ones to the embodiments of the method for identifying a user on a exercise equipment and the related system described above in order to meet incidental needs, without departing from the scope of the following claims. Each of the features described as belonging to a possible embodiment can be obtained independently of the other embodiments described.

The invention claimed is:

1. A method for identifying a user on an exercise equipment, comprising:

acquiring, using an electronic portable device of the user, an equipment identification code (IDE) comprising static information uniquely identifying a specific piece of exercise equipment;

sending, from the electronic portable device, the equipment identification code (IDE) to an electronic calculator;

sending, from the electronic portable device, a user identification code (IDU) identifying a specific user to the electronic calculator;

receiving and storing, in the electronic calculator, user operative data (UOD) comprising user personal data (UDP) of the specific user identified by the user identification code (IDU), a training program (TP) of the specific user identified by the user identification code (IDU), and training data (TD) of the specific user identified by the user identification code (IDU); and sending, from the electronic calculator, on the basis of both the equipment identification code (IDE) identifying the specific piece of exercise equipment and the user identification code (IDU) identifying the specific user, the user operative data (UOD) of the specific user identified by the user identification code (IDU) to the specific piece of exercise equipment identified by the equipment identification code (IDE).

2. The method of claim 1, further comprising manually setting up, by the user, the training program (TP) on the exercise equipment on which the user has been identified.

3. The method of claim 1, the method further comprising automatically setting up, by means of the exercise equipment, the training program (TP).

4. The method of claim 3, wherein automatically setting up comprises sending to the exercise equipment, by means of the electronic calculator, on the basis of the equipment identification code (IDE) associated to the exercise equipment and the user identification code (IDU) received from the electronic portable device, the training program (TP) assigned to the user corresponding to the user identification code (IDU).

5. The method of claim 1, further comprising sending to the electronic calculator, on the basis of the user identification code (IDU), the training data (TD) of the user.

6. The method of claim 5, further comprising storing, by means of the electronic calculator, the training data (TD) of the user into an area of the memory unit of the electronic calculator which is reserved to the user having the user identification code (IDU).

7. The method of claim 6, comprising sending to the electronic portable device of the user, by means of the electronic calculator, on the basis of the user identification code IDU, the training data (TD) of the user.

8. The method of claim 1, further comprising updating, by means of the electronic calculator, on the basis of the user identification code (IDU), the user personal data (UPD).

9. The method of claim 8, wherein the user operative data (UOD) comprises updated user personal data (UUPD), the step of updating further comprising sending to the electronic calculator, by means of the exercise equipment, on the basis of the user identification code (IDU), the updated user personal data (UUPD).

10. The system of claim 9, wherein the exercise equipment is configured to send to the electronic calculator, on the basis of the user identification code (IDU), the training data (TD) of the user.

11. The system of claim 10, wherein the electronic calculator is configured to send to the electronic portable device of the user, on the basis of the user identification code (IDU), the training data (TD) of the user.

12. System for identifying a user on an exercise equipment, comprising:

an exercise equipment having a respective equipment identification code (IDE) comprising static information uniquely identifying a specific piece of exercise equipment;

a electronic calculator operatively connected to the exercise equipment;

a electronic portable device comprising, stored in a memory unit, a user identification code (IDU) identifying a specific user, the electronic portable device being configured to acquire the equipment identification code (IDE) from the exercise equipment, the electronic portable device being further configured to send the equipment identification code (IDE) to the electronic calculator and to send the user identification code (IDU) to the electronic calculator;

wherein the electronic calculator is configured to send to the exercise equipment, on the basis of both the equipment identification code (IDE) identifying the specific piece of exercise equipment and the user identification code (IDU), user operative data (UOD), the user operative data (UOD) comprising user personal data (UDP) of the specific user identified by the user identification code (IDU), a training program (TP) of the specific user identified by the user identification code (IDU), and training data (TD) of the specific user identified by the user identification code (IDU).

13. The system of claim 12, wherein the exercise equipment is directly set up by the user with the training program by means of an interactive user interface of a control station of the exercise equipment.

14. The system of claim 12, wherein, the electronic calculator being configured to send to the exercise equipment, on the basis of the user identification code (IDU), the user personal data (UPD).

15. The system of claim 14, wherein the user operative data (UOD) comprises updated user personal data (UUPD), the exercise equipment being configured to send to the electronic calculator, on the basis of the user identification code IDU, the updated user personal data (UUPD).

16. A non-transitory program product loadable in a memory unit of an electronic portable device of a user, the non-transitory program product being executed by a data processing unit of the electronic portable device to perform:
  acquiring an equipment identification code (IDE) comprising static information uniquely identifying a specific piece of exercise equipment;
  sending the equipment identification code (IDE) to an electronic calculator;
  sending a user identification code (IDU) identifying a specific user to the electronic calculator;
  wherein the program product is executed by the data processing unit of the electronic portable device to perform also the step of receiving from the electronic calculator, on the basis of both the equipment identification code (IDE) and the user identification code (IDU), user operative data (UOD), said user operative data (UOD) comprising user personal data (UDP) of the specific user identified by the user identification code (IDU), a training program (TP) of the specific user identified by the user identification code (IDU), and training data (TD) of the specific user identified by the user identification code (IDU).

17. The non-transitory program product of claim 16, wherein the program product is executed by the data processing unit of the electronic portable device to also perform the step of receiving from the electronic calculator, on the basis of the equipment identification code (IDE), equipment instruction data (EID).

18. A non-transitory program product loadable in a memory unit of an electronic calculator, the program product being executed by a data processing unit of the electronic calculator to perform sending to an exercise equipment, on the basis of both an equipment identification code (IDE) comprising static information uniquely identifying a specific piece of exercise equipment and an user identification code (IDU) identifying a specific user, user operative data (UOD) the user operative data (UOD) comprising user personal data (UDP) of the specific user identified by the user identification code (IDU), a training program (TP) of the specific user identified by the user identification code (IDU), and training data (TD) of the specific user identified by the user identification code (IDU).

19. The non-transitory program product of claim 18, wherein the program product is executed by the data processing unit of the electronic calculator to perform also the step of receiving from an electronic portable device, on the basis of both the equipment identification code (IDE) and the user identification code (IDU), updated user personal data (UUPD).

20. The non-transitory program product of claim 18, wherein the program product is executed by the data processing unit of the electronic calculator to also perform the step of sending to an electronic portable device, on the basis of the equipment identification code (IDE), equipment instruction data (EID) which explains how the exercise equipment operates.

* * * * *